United States Patent

Sleep

[11] Patent Number: 5,188,605
[45] Date of Patent: Feb. 23, 1993

[54] SEPARABLE INSERTION TOOL
[75] Inventor: Richard F. Sleep, Miami, Fla.
[73] Assignee: Cordis Corporation, Miami, Fla.
[21] Appl. No.: 697,114
[22] Filed: May 8, 1991
[51] Int. Cl.⁵ .................................................. A61M 5/178
[52] U.S. Cl. ................................... 604/158; 604/160; 604/167
[58] Field of Search ............... 604/167, 164, 161, 160, 604/170, 171, 264, 158

[56] References Cited
U.S. PATENT DOCUMENTS

| | | | |
|---|---|---|---|
| 3,550,591 | 12/1970 | MacGregor | 604/161 |
| 4,175,564 | 11/1979 | Kwak | 604/171 |
| 4,306,562 | 12/1981 | Osborne | 604/164 X |
| 4,354,491 | 10/1982 | Marbry | 604/161 X |
| 4,402,685 | 9/1983 | Bühler et al. | 604/164 X |
| 4,412,832 | 11/1983 | Kling et al. | 604/164 |
| 4,569,347 | 2/1986 | Frisbie | 604/164 X |
| 4,626,245 | 12/1986 | Weinstein . | |
| 4,798,594 | 1/1989 | Hillstead . | |
| 5,078,700 | 1/1992 | Lamb et al. | 604/264 |

FOREIGN PATENT DOCUMENTS 0021446 3/1982 European Pat. Off. .

Primary Examiner—John J. Wilson
Assistant Examiner—Jeffrey A. Smith
Attorney, Agent, or Firm—Watts, Hoffmann, Fisher & Heinke Co.

[57] ABSTRACT

A catheter insertion tool for the insertion of fragile catheters through a hemostatic valve without damage to the fragile catheter. The catheter insertion tool includes a manipulator body with a "V" slot narrowing to a line of weakness that extends the length of both the manipulator body and attached tubular portion. In the preferred embodiment of the catheter insertion tool the line of weakness is a slit extending through the wall of the catheter extension tool.

3 Claims, 1 Drawing Sheet

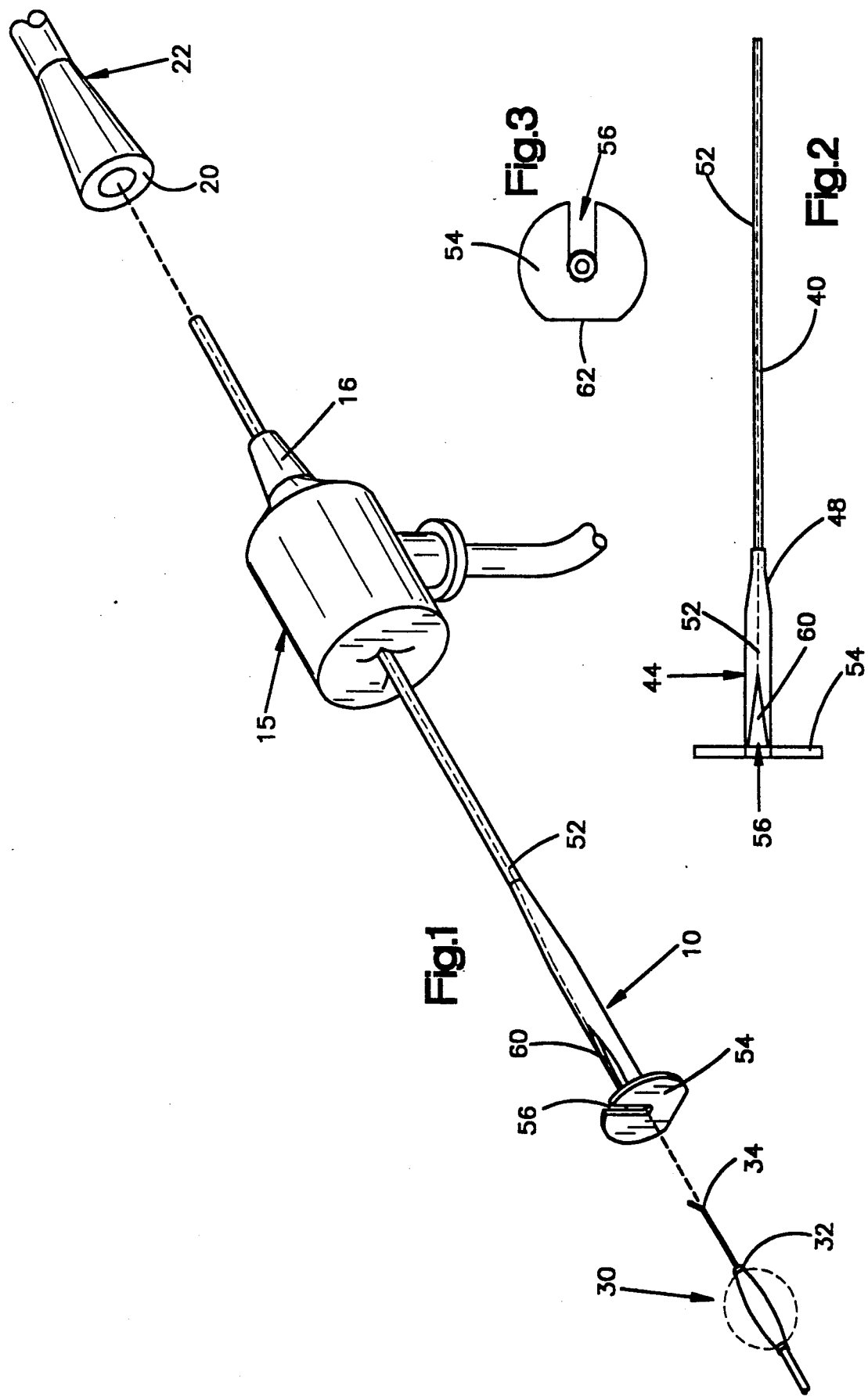

SEPARABLE INSERTION TOOL

TECHNICAL FIELD

The present invention relates to guide catheters and catheter insertion devices. More particularly, the invention relates to a catheter insertion device that can be used to insert a dilation catheter or other fragile catheter into a subject. After insertion of the dilation catheter into a guide catheter, the catheter insertion device can be removed and separated from the catheter by splitting it along a score line.

BACKGROUND ART

The use of introducer catheters, balloon catheters and similar devices in cardiology is well known. Often an introducer catheter is used to guide the balloon catheter. The introducer catheter includes a hemostasis valve at its proximal end for preventing blood loss when the introducer catheter is placed in an artery. An example of an improved hemostasis valve is described in U.S. Pat. No. 4,798,594 to Hillstead and is incorporated by reference. Since less blood is lost with the improved hemostasis valve, the need for blood transfusions is reduced and the chances of contracting AIDS, hepatitis and other blood-borne diseases is lessened.

A problem with the new hemostasis valve is in the insertion of the guide wire and balloon catheter through the hemostasis valve without damage to the guide wire or balloon catheter. Cardiologists often will bend the tip of the guide wire and of a balloon catheter to a preselected angle to ease insertions of the balloon catheter into the artery to be opened. When the cardiologist inserts the guide wire and balloon catheter through the hemostasis valve, the bend in the tip of the guide wire may change, making the task of correctly positioning the balloon catheter more difficult, if not impossible.

A catheter insertion device for use with an introducer catheter is described in U.S. Pat. No. 4,569,347 to Frisbie. Frisbie's catheter insertion device utilizes a helically or spirally cut tubular member and a pull member attached to the tubular member. The pull member is provided on one end of the tubular member to facilitate removal of the catheter insertion device from the hemostatic valve of the introducing catheter.

The Frisbie catheter insertion device is inserted through the hemostasis valve with either a mandrel or a dilation catheter inside the insertion device to make the insertion device stiff. If a mandrel is used, the mandrel is withdrawn after the catheter insertion device is inserted through the hemostasis valve. Once the mandrel is removed, the balloon or dilation catheter can be pushed through the catheter insertion device and into the guide catheter. Once the catheter introducing device and dilation catheter is inserted through the hemostasis valve, the catheter insertion device can be separated from the hemostasis valve, unwound and pulled away from the dilation catheter.

Other insertion devices for use with transfusion catheters or cardiac electrodes have been described by Bühler in West German Patent 2,026,572, Kling in U.S. Pat. No. 4,412,832 and Osborne in U.S. Pat. No. 4,306,562.

Bühler describes a dividable, short, plastic catheter that can be produced in an extrusion process. Bühler's catheter uses two polymers, such as polyethylene and polypropylene, that are insoluble with one another. When the catheter is extruded, two lengthwise strips of one polymer displaced by about 180° are embedded into the catheter formed from the other polymer to form two longitudinal lines of weakness. The catheter is described as being used as an auxiliary device for the introduction of a longer, flexible infusion catheter into a patient.

Kling's introducer catheter has longitudinal scored lines of weakness on the catheter tube along which the catheter can be split. Tabs serve as grips which facilitate the splitting of the catheter. The introducer catheter is described as an "over-the-needle" type in which the introducer catheter is telescopically mounted over a hypodermic needle. The needle is removed after insertion of the introducer catheter into the patient and a pliant infusion catheter is introduced through the lumen of the introducer catheter. Once the infusion catheter is in place, the introducer catheter is withdrawn from the patent and then peeled apart from the infusion catheter. A slidable sleeve on Kling's introducer catheter can be sutured to the patent to support the infusion catheter.

Osborne, in U.S. Pat. No. 4,306,562, describes a flexible cannula for use in inserting pacemaker electrodes. The cannula itself is similar to Kling's introducer catheter. One difference between Osborne's cannula and Kling's catheter is that the Osborne cannula does not have a slidable sleeve on the cannula.

DISCLOSURE OF THE INVENTION

The present invention relates to an insertion device for inserting fragile catheters or guide wires into a guide catheter. The insertion device has a tubular manipulator with an extension at one end which can be pushed on as the insertion device is installed and pulled on to remove the insertion device from the guide catheter. The manipulator is connected to a tubular member having a blunt tip. Both the manipulator and the tubular member have an aligned line of weakness along the length of the catheter insertion device.

After a balloon catheter is inserted into the guide catheter through the catheter insertion device, the insertion device is split along the line of weakness to free the insertion device from the balloon catheter. The tubular member has increased longitudinal rigidity which allows insertion through a hemostasis valve without fear of buckling of the catheter insertion device or resort to a stiffening tube or mandrel.

In another aspect of the invention, the manipulator has an open slot extending along a manipulator body that narrows in a "v" shape as the slot extends down the manipulator body towards the tubular extension. This "v" shaped slot allows the physician to easily thread a balloon catheter into the catheter insertion tool without damaging a preformed bend in the guide wire. If the longitudinal line of weakness extends from the end of the "v" shaped slot to the tip of the catheter insertion device, the "v" shape of the slot focuses the tearing or separation force on the line of weakness at the end of the slot.

The preferred materials for making the catheter insertion tool are polyethylene and/or polypropylene. These plastics have the advantage of being readily extruded and injection molded without the use of lubricants in the extrusion or molding processes. The additional advantage of polyethylene and polypropylene is that the crystalline structure of the polymer can be oriented by the extrusion process along the longitudinal axis of the catheter insertion tool. The aligning of the crystalline structure will also aid in obtaining a clean tear along the line of weakness.

In one embodiment, a one-piece catheter insertion device is formed by extruding a tubular member and then molding this member to form a one-piece insertion device. This embodiment would have the advantage of decreased production costs since the step of connecting the manipulator body to the tubular member is avoided.

BRIEF DESCRIPTION OF THE DRAWINGS

FIG. 1 illustrates the catheter insertion tool extending through a hemostasis valve and a distal end of a balloon catheter and guide wire 5 and the guide catheter 30;

FIG. 2 is a plan view of a catheter insertion tool oriented to illustrate a longitudinal line of weakness; and FIG. 3 is an elevation view of a proximal end of the insertion tool.

BEST MODE FOR CARRYING OUT THE INVENTION

FIG. 1 is a perspective view showing an insertion tool 10 constructed in accordance with the invention being inserted through a hemostasis valve 15 such as a valve constructed in accordance with the teachings of U.S. Pat. No. 4,798,594 to Hillstead. The hemostasis valve 15 defines a through passage that extends through a tapered region 16 of the valve which engages a proximal end 20 of an introducing or guide catheter 22. The guide catheter 22 allows a balloon catheter 30, for example, to be inserted into a subject, routed to the vicinity of an artery blockage and used to re-institute or improve blood flow through the region of the blockage.

The balloon catheter 30 includes a distal end 32 that defines an opening which can deliver radio-opaque material through the balloon catheter into the subject blood vessel to facilitate imaging of the blood vessel on a viewing screen. As depicted in FIG. 1, a guide wire 34 has been inserted through the balloon catheter and bent into a predetermined configuration to facilitate positioning the balloon catheter after it is routed through the guide catheter 22. Use of the insertion tool 10 reduces the probability of damage to the guide wire tip 34 or balloon catheter 30 as the balloon catheter's distal tip is pushed through the hemostasis valve 15.

As depicted in FIGS. 1, 2 and 3, the introducing tool 10 includes an elongated first tube 40 having a diameter sufficient to accommodate the balloon catheter. In the preferred embodiment of the invention the tube 40 is extruded and has an inner diameter of 0.038 inches. Attached at a proximal end of the first tube 40 is an enlarged tube 44 having a tapered or transition region 48. In accordance with the preferred embodiment of the invention, the tubes 40, 44 are separate pieces that are connected during fabrication of the insertion tool using ultrasonic welding techniques well known in the prior art.

The enlarged tube 44, as well as the tube 40, define a line of weakness 52 extending along the length of the insertion tool 10 that is preferably a slit completely through a wall of the catheter insertion tool. Attached to the proximal end of the tool 10 is a manipulator 54 having a slot 56 to accommodate insertion of the balloon catheter 30 and guide wire 34. The enlarged tube 44 and manipulator 54 are injection molded in a single mold and physically connected to the tube 40 by ultrasonic welding. Aligned with the line of weakness 52 in the enlarged tube 44 is a "v" shaped notch 60 that narrows to the line of weakness 52.

As seen in FIG. 3, the manipulator 54 is generally circular with the slot 56 extending from an outer circumference of the manipulator 54 to a center region. The manipulator 54 also defines a flattened portion 62 opposite the slot 56.

OPERATION

In operation, the hemostasis valve 15 is separated from the guide catheter 22 and the tube 40 inserted through the hemostasis valve as depicted in FIG. 1. The hemostasis valve can then be connected to the proximal end of the guide catheter 22 and the balloon catheter 30 and guide wire 34 inserted through the insertion device or tool 10 into the guide catheter. Once the delicate, easily damaged distal portions of the guide wire and balloon catheter have been routed through the hemostasis valve, the insertion tool 10 can be separated from the hemostasis valve. The elongated body of the balloon catheter has sufficient strength to be pushed through the hemostasis valve 15 as the distal end 32 passes through the guide catheter 22 to a region of interest within the subject.

The tool 10 is separated from the valve 15 and balloon catheter 30 by exerting a sideward force against the tool 10 by means of the manipulator 54. The attending physician grasps the manipulator 54 and bends the tool 10 away from the unstressed position of FIG. 1 so that a slot or opening occurs along the line of weakness 52. As the slot opens, the physician peels the insertion tool away from the balloon catheter while withdrawing the tool 10 from the hemostasis valve. This allows the insertion tool 10 to be completely separated from the hemostasis valve and balloon catheter so that the insertion tool can be discarded.

In accordance with an alternate technique, instead of mating the hemostasis valve 15 with the guide catheter 22, it is possible to insert the balloon catheter into the insertion tool and through the hemostasis valve before mating the valve with the guide catheter. This allows the insertion tool to be separated from the valve by applying a sideward force with the manipulator before the hemostasis valve even engages the guide catheter. It is possible, therefore, that the hemostasis valve and balloon catheter be ready for mating with the guide catheter 22 even before the guide catheter is positioned within the subject. Thus, the steps of inserting the balloon catheter are accomplished by first inserting the guide catheter using techniques well known in the prior art and immediately inserting the hemostasis valve with accompanying balloon catheter into the guide catheter and securing the hemostasis valve to the proximal end of the guide catheter. The balloon catheter is then pushed through the hemostasis valve until its distal end extends beyond the end of the guide catheter and combined movement of the balloon catheter and guide wire allow accurate positioning of the balloon in preparation for treatment of a blood vessel.

The preferred insertion tool has been described with a degree of particularity. It is the intent, however, that the invention include all modifications or alterations from the disclosed insertion tool's design following within the spirit or scope of the appended claims.

I claim:

1. Apparatus for inserting a catheter into a guide catheter comprising:

a. an elongated polyethylene tube having a slit along its length that extends through a wall of the elongated polyethylene tube;

b. an enlarged polyethylene tube having a notch for accepting a catheter's distal tip and routing the distal tip through the elongated polyethylene tube into the guide catheter; said notch narrowing to a slit that extends through a wall of said enlarged polyethylene tube along a tapered region at a distal end where the enlarged polyethylene tube narrows to a reduced diameter and is connected to the elongated polyethylene tube; and c. a polyethylene manipulator attached to a proximal end of the enlarged polyethylene tube having a slot extending from its outer circumference to a center region that opens into the notch in the enlarged polyethylene tube.

2. The apparatus of claim 1 wherein the manipulator elongated polyethylene tube and enlarged polyethylene tube are formed form one piece of polyethylene.

3. Apparatus for inserting a catheter into a guide catheter comprising:

a. an elongated polyethylene tube having a line of weakness along its length;

b. an enlarged polyethylene tube having a notch at its proximal end that narrows to a line of weakness along its longitudinal axis which extends along a tapered region at its distal end; and c. a polyethylene manipulator, having a slot extending from its outer circumference to a center region, wherein:

i. a proximal end of the elongated polyethylene tube is attached to the distal end of the enlarged polyethylene tube;

ii. the manipulator is attached to the proximal end of the enlarged polyethylene tube; and iii. the longitudinal line of weakness of the elongated polyethylene tube is aligned with the longitudinal line of weakness in the enlarged tube and with the manipulator slot.

* * * * *